United States Patent [19]

Abell et al.

[11] Patent Number: 5,405,319

[45] Date of Patent: Apr. 11, 1995

[54] BOWEL EVACUATION SYSTEM

[76] Inventors: Roy Abell, 4809 Riverview Way, Duluth, Ga. 30136; Thomas Shilling, 3160 S. Acoma St., Englewood, Colo. 80110

[21] Appl. No.: 176,097

[22] Filed: Dec. 30, 1993

[51] Int. Cl.6 .................... A61M 1/00; A61M 5/178; A61M 5/00

[52] U.S. Cl. ....................... 604/27; 604/34; 604/36; 604/37; 604/250

[58] Field of Search .............. 604/27, 28, 30, 33, 604/34, 36, 37, 246, 249, 250, 275; 251/5; 137/630.16

[56] References Cited

U.S. PATENT DOCUMENTS

| | | | |
|---|---|---|---|
| 493,208 | 3/1893 | Cruickshank | 604/36 |
| 790,353 | 5/1905 | Estlingen | 604/34 |
| 818,144 | 4/1906 | Bosworth | 604/37 |
| 867,445 | 10/1907 | Thayer | 604/37 |
| 906,711 | 10/1907 | Hill et al. | |
| 972,201 | 11/1909 | Kussart. | |
| 1,042,549 | 1/1912 | Goff. | |
| 1,217,692 | 4/1916 | Bookman. | |
| 1,317,851 | 10/1919 | Arnett | 604/34 |
| 1,588,032 | 9/1924 | Klaiber. | |
| 2,133,626 | 9/1936 | Mayberry | 128/227 |
| 2,252,569 | 8/1941 | Kennison | 128/227 |
| 2,955,596 | 4/1959 | Knoch | 128/251 |
| 3,004,537 | 12/1958 | Turliuc | 128/227 |
| 3,398,743 | 8/1968 | Shalit | 604/36 |
| 4,186,740 | 2/1980 | Guerra | 604/250 |
| 4,504,270 | 3/1983 | Miller | 604/275 |
| 5,186,431 | 2/1993 | Tamari | 251/5 |
| 5,197,950 | 3/1993 | Clayton | 604/28 |

Primary Examiner—John D. Yasko
Assistant Examiner—Frank Wilkens, III
Attorney, Agent, or Firm—John E. Reilly

[57] ABSTRACT

A portable, lightweight bowel evacuation system is made up of a water bag which is elevated above the patient with a check valve in the delivery line from the water bag into a rectal insertion tube or speculum, a drain line leading from the speculum includes a disposable valve member for selectively opening and closing the drain line, and one or more pressurizing members in the form of manual squeeze bulbs are provided to simultaneously open the check valve for delivery of water from the water bag through the speculum and close the drain valve while the check valve is open and further is open to simultaneously close the check valve when the drain is opened. In a modified form, a flow control valve in communication with a source of air under pressure takes the place of the manual squeeze bulb to control opening and closing of the valve members.

32 Claims, 3 Drawing Sheets

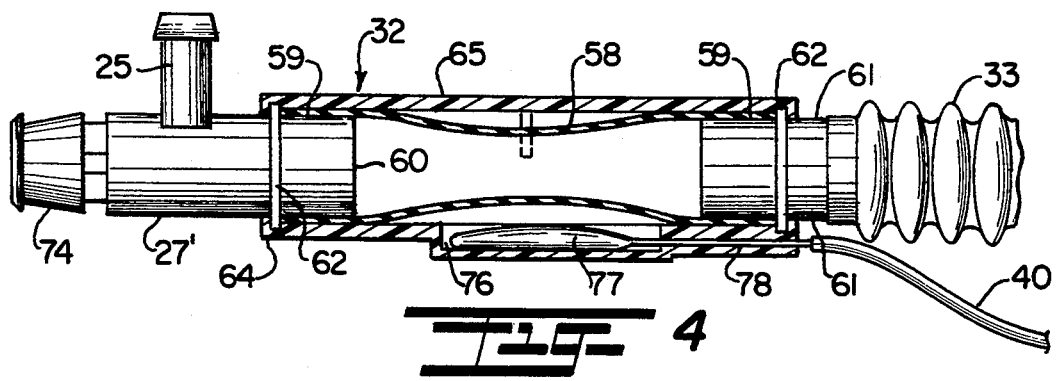
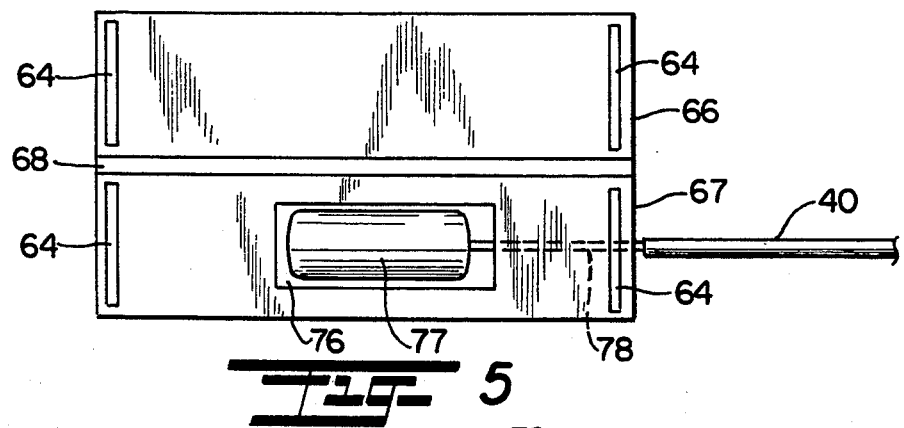
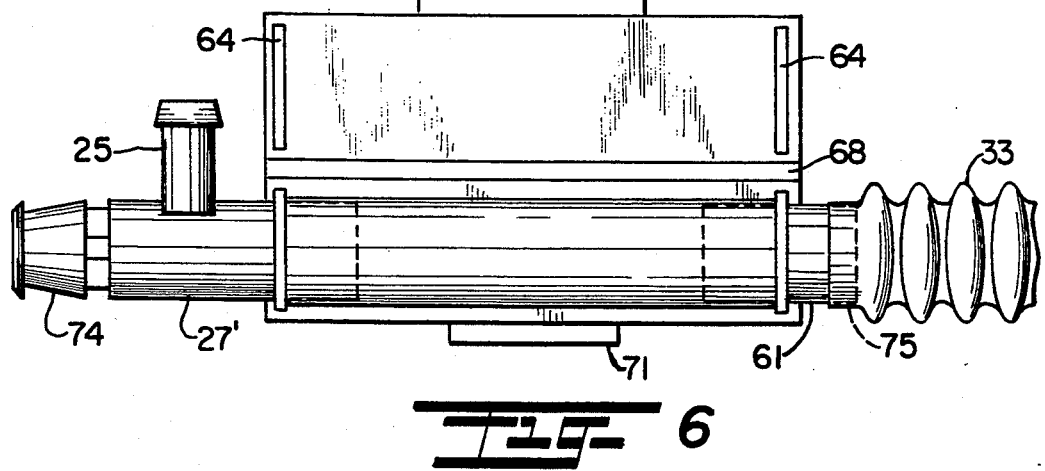

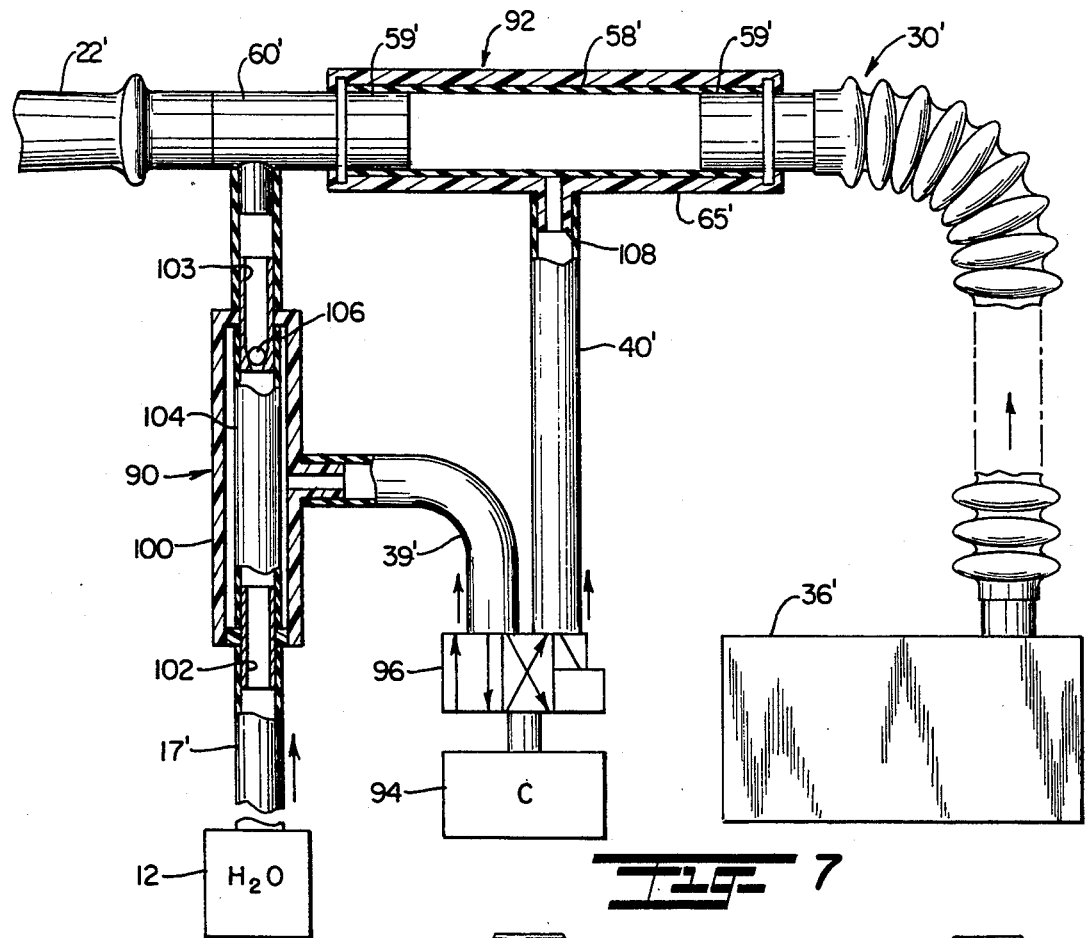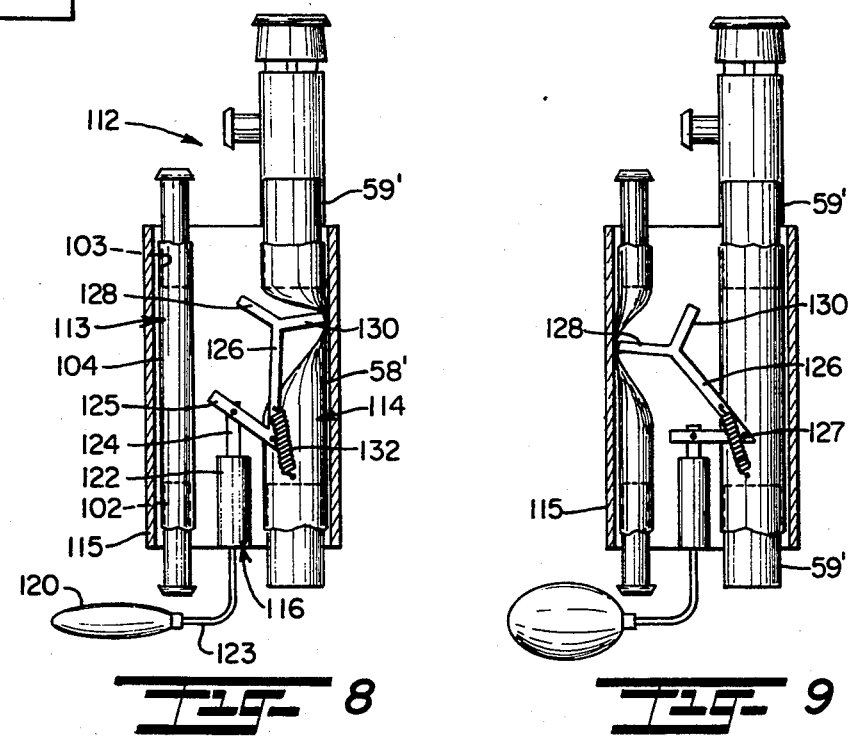

BOWEL EVACUATION SYSTEM

This invention relates to bowel evacuation systems; and more particularly relates to a novel and improved method and apparatus for the removal of waste material from the colon.

BACKGROUND AND FIELD OF INVENTION

In colonic lavage systems, it is customary to employ fairly sophisticated pumping devices for pumping water at a predetermined pressure level through a speculum into the colon and which will, automatically in response to a predetermined pressure level, close a valve between the speculum and pumping system while opening another valve to permit water and waste material to drain through a drain hose into a suitable collection container. A system of this type is set forth and disclosed in U.S. Pat. No. 5,019,056 assigned to the assignee of this invention.

In the past, systems have been devised which minimize the requirement for sophisticated pumping systems. For example, U.S. Pat. No. 2,133,626 to F. A. Mayberry is directed to a portable colonic irrigator which employs gravity flow from a syringe bag under the control of a check valve and manually operated valve in a line which leads to an irrigating tube. U.S. Pat. No. 1,588,032 to A. Klaiber is directed to a system for the medical treatment of the intestines in which an air bulb is employed to inject air into a hose leading from a tank containing a medicinal compound. U.S. Pat. No. 1,042,549 to S. B. Goff employs pressure bulbs to direct water from a supply tank into nozzles in a bidet. U.S. Pat. No. 972,201 to J. Kussart discloses a syringe in which bulb pressure activates valves with one bulb operating to force liquid through a nozzle and the other to withdraw liquid from the cavity. U.S. Pat. No. 3,771,552 to Waysilk et al relies upon gravity feed to direct water into the patient. Other representative patents are U.S. Pat. Nos. 906,711 to M. Hill et al, 1,217,692 to J. B. Bookman, 2,252,569 to R. S. Kennison, 2,955,596 to M. H. Knoch, 3,004,537 to R. Turliuc and 4,504,270 to R. E. Miller.

There is a need for a simplified colonic lavage system which does not require a sophisticated, bulky pumping system and which can result in a highly portable, lightweight system containing a minimum number of parts and which is under the complete control of the patient or operator at all times.

SUMMARY OF INVENTION

It is therefore an object of the present invention to provide for a novel and improved method and apparatus for the removal of waste matter from the colon.

It is another object of the present invention to provide for a novel and improved colonic lavage system which is simple and efficient to manufacture, assemble and use.

A further object of the present invention is to provide for a colonic lavage system which is portable, lightweight and wherein those portions exposed to waste are disposable and easily replaced.

It is a still further object of the present invention to provide for a colonic lavage system which enables complete control over injection of water into the colon and removal of waste from the colon through one or more manually operated pressurizing devices, such as, a bellows or squeeze bulb; and further wherein a novel and improved valve member is responsive to the pressurizing device to closely control the delivery of water into the colon.

It is an additional object of the present invention to provide for a novel and improved colonic lavage system which may either be manually or automatically controlled to regulate the flow rate and pressure of water delivered into the colon according to individual requirements and comfort levels.

In accordance with the present invention, a preferred form of bowel evacuation apparatus comprises a source of water under pressure including a delivery line and first valve means for opening and closing the delivery line, a rectal insertion tube in communication with the delivery line for directing water from the water source into the colon, a drain line in communication with the tube including second valve means for selectively opening and closing the drain line, and valve control means for simultaneously controlling the first and second valve means in order to open the first valve means for the delivery of water from the water source through the rectal insertion tube and to close the second valve means while the first valve means is open. The valve control means is further operative to simultaneously close the first valve means and open the second valve means to prevent water from flowing from the water source into the rectal insertion tube when water and waste material are being extracted from the colon. Those parts of the system which are exposed to waste materials including the rectal insertion tube, drain line and collection bag may be replaced when desired without replacing the other parts of the system. The entire system is extremely lightweight, compact and can be conveniently stored within a box, and the box may be used to retain the collection bag and then be discarded with the other disposable components when desired.

In the preferred form of invention, the valve control means takes the form of at least one manual pressurizing member, such as, a squeeze bulb for simultaneously controlling first and second valve means. In modified forms of invention, the valve control means may take the form of a pair of squeeze bulbs; or a flow control valve may be associated with a source of air under pressure to selectively pressurize the first or second valve means.

Another modified form of invention employs a dual valve assembly with a common actuator to simultaneously control opening and closing of the first and second valve means.

The above and other objects of the present invention will become more readily appreciated and understood from a consideration of the following detailed description of preferred and modified forms of the present invention when taken together with the accompanying drawings in which:

BRIEF DESCRIPTION OF THE DRAWINGS

FIG. 4 is a view partially in section of a preferred form of valve member employed on the drainage side of the system;

FIG. 5 is a plan view of the valve casing for the valve of FIG. 4 with the casing illustrated in an open position;

FIG. 6 is another plan view of the valve assembly shown in FIG. 4 with the casing shown in an open position;

FIG. 7 is a somewhat schematic view of a modified form of the present invention provided with an automatic pressure control unit;

FIG. 8 is a somewhat schematic view of an alternate form of valve assembly with common actuator disposed in a position opening the first valve means and closing the second valve means; and FIG. 9 is another schematic view of the alternate form of valve assembly shown in FIG. 8 with the actuator disposed in a position closing the first valve means and opening the second valve means.

DETAILED DESCRIPTION OF PREFERRED EMBODIMENT

Figure 1:
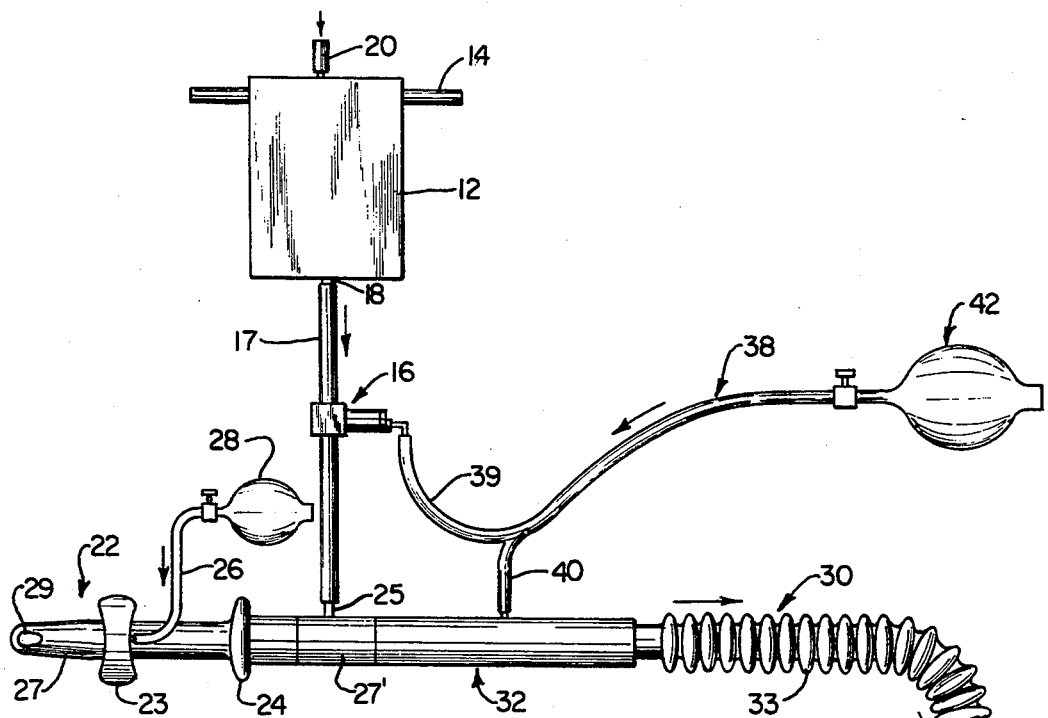
FIG. 1 is a somewhat schematic illustration of a preferred form of bowel evacuation system in accordance with the present invention.
Figure 1:
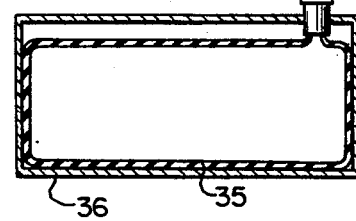
Figure 3:
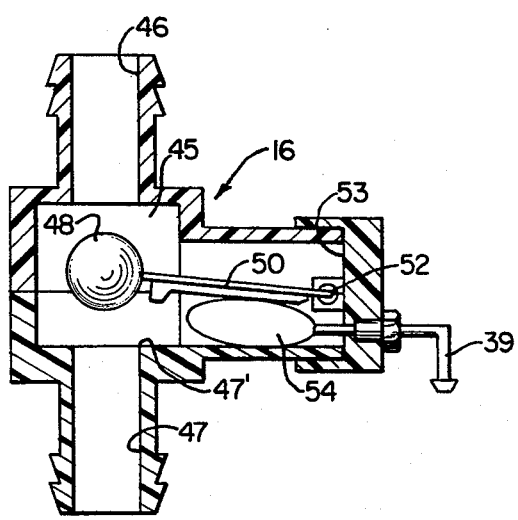
FIG. 3 is a sectional view of the valve member illustrated in FIG. 2 but shown in an open position.
Figure 2:
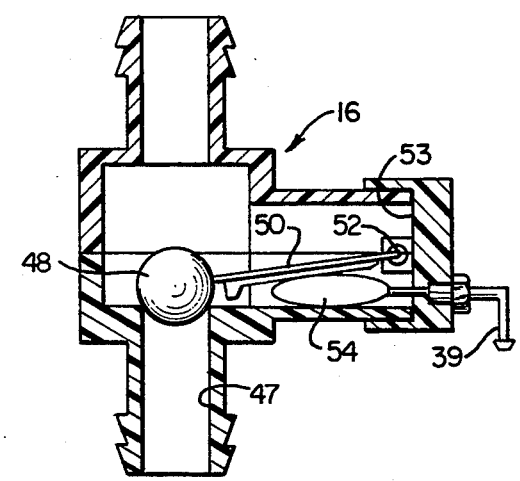
FIG. 2 is a cross-sectional view of a valve member forming a part of the system with the valve shown in a closed position.

A preferred form of bowel evacuation apparatus 10 is broadly comprised of a source of water under pressure defined by a water bag 12 having a rope or other suspension member 14 in order to hang the bag from a stand, not shown, at an elevated height above the patient for gravity flow of water from the bag 12. Typically, the water bag is placed approximately 2' over a bed or other surface upon which the patient lies. A check valve 16 is positioned in a hose 17 leading from an outlet port 18 at the lower end of the bag, the check valve controlling the flow or delivery of water from the water bag in a manner to be described. An inlet port 20 is disposed at the upper end of the bag for introduction of water into the bag.

A rectal insertion tube or speculum 22 is of conventional construction, such as, that set forth and described in U.S. Pat. No. 5,019,056 and has an inflatable cuff 23, a collar 24 and inlet port 25 at rear end portion 27' of the tube 22 for connection of the hose 17. An air line 26 extends into communication with the interior of the cuff 23 so as to permit inflation of the cuff by applying air under pressure with the aid of a manual pressurizing member in the form of a squeeze bulb 28. For purposes of the present invention, the speculum 22 is insertable into the anal canal of the patient and includes a tapered end portion provided with diametrically opposed eyelets 29 and an elongated tubular body 27 which tapers rearwardly and terminates in the connecting end portion 27' which is coupled to a drain line 30.

The waste disposal or drain line 30 extends from the end portion 27' of the tube 22 and includes a valve member 32 and a hose 33 extending from the valve 32 into a collection area defined by a collection bag 35 contained within a collection box 36.

In order to control opening and closing of the valve members 16 and 32, an air pressure line 38 has one branch 39 leading to the valve member 16 and a second branch 40 leading to the valve 32. Air pressure to the valve members is controlled by a pressurizing member in the form of a squeeze bulb 42 which when manually squeezed will simultaneously deliver air under pressure to both of the valves 16 and 32, causing the valve 16 to open and the valve 32 to close. The bulb 42 is compressed for a time interval sufficient for water to flow from the water bag 12 into the patient and to fill the colon. When the bulb 42 is released, its resiliency is such that it will automatically return to its original shape thereby creating a vacuum sufficient to remove the air pressure from the valves 16 and 32 whereupon the valve 16 will return to a closed position and the valve 32 will return to an open position.

A preferred form of valve member 16 includes a generally tubular valve body 44 defining an interior chamber 45 located intermediately between coaxial inlet and outlet ports 46 and 47 with a valve seat 47' formed at the intersection of the outlet port 47 with the chamber 45. A valve element 48 is disposed in the chamber and is in the form of a ball or sphere mounted at the free end of a pivot arm 50, the opposite end 52 of the arm 50 being pivotally connected to end wall 53 of the valve body. An actuating member in the form of an inflatable bag 54 is disposed beneath the arm 50, and the air line 39 extends through the end wall 53 into communication with the interior of the bag 54. The bag 54 bears against the underside of the pivot arm and, when inflated by application of air under pressure through the branch line 39 by the squeeze bulb 40, will raise the arm 50 and attached ball 48 away from the valve seat to open the valve and permit the gravity flow of water from the water bag 12 through the hose 17 into the insertion tube 22. When air pressure is relieved in the branch line 39 and in the inflatable bag 54, the weight of the pivot arm 50 will cause the valve element 48 to move into engagement with the valve seat 47' and close the valve against further flow. The design of the valve member 16 is such that: a relatively small pressure level is required to inflate the bag and may be on the order of one to two psi. As a suitable alternative to the use of the inflatable bag 54, the actuating member may be an air cylinder disposed in the space occupied by the bag 54 with a push rod moving upwardly from beneath the arm 50 and which is responsive to air pressure applied by the squeeze bulb 42 to control opening and closing of the check valve; and if desired a spring just above the push rod and the arm 50 may be employed to return the valve to the closed position when no air pressure is applied to the cylinder if the weight of the arm 50 is not sufficient to return the valve to the closed position.

As shown in more detail in FIGS. 4 to 6, the valve 32 comprises an elastomeric tubular liner 58 having opposite ends 59 stretched over tubular extremities 60 and 61 of the end portion 27' and hose 33, respectively. Each portion 60 and 61 has a circular flange 62 sized to fit into diametrically opposed grooves 64 in an outer, hollow elongated valve body 65. Preferably, the body 65 is made up of two hollow, semi-cylindrical halves 66 and 67 interconnected along confronting lengthwise edges of the body by a living hinge 68 so that the halves may be hinged between an open position as illustrated in FIGS. 5 and 6 and a closed position illustrated in FIG. 4. In the closed position, the circular flanges 62 at opposite ends of the liner 58 are wedged into the grooves 64 at opposite ends of the outer body 65. Complementary latch portions 70 and 71 disposed along free edges of the halves 66 and 67 are brought into engagement with one another when the halves are folded together into the closed position so as to securely but releasably lock the halves together and retain the liner 58 in position within the body 65.

A releasable coupler 74 completes the connection of the connecting end portion 27' of the speculum 22 to the speculum 22, and the inlet port 25 serves to connect the delivery hose 17 into the cuff 23. Another coupling 75 at the opposite end portion 61 serves to connect the hose 33 into the valve 32. In order to control movement of the valve 32 between an open and closed position, one of the halves 66 includes a shallow compartment 76 on its interior surface to receive an inflatable bag 77 with an air line 78 extending from the bag through the wall of the half 66 into communication with the branch line 40. When the bulb 42 is pressurized or squeezed, air under pressure is delivered into the bag 77 to expand into engagement with one wall of the liner 58 and cause the liner to be constricted or pinched off at that point to close the valve 32 and prevent the flow of water therethrough. When pressure is relieved by releasing the bulb 42, the differential pressure resulting from the flow of water and waste material from the colon will cause the liner to open and permit removal of the water and waste material through the drain line 30 into the collection bag 35. Any slight differential pressure existing between the colonic pressure and pressure exteriorly of the liner will be sufficient to open the valve 32.

In practice, the water bag 12 is suspended in an elevated position above the patient and filled with body temperature water. A suitable clamp, not shown, can be employed to close the lower outlet end of the bag 12. The height of the bag 12 is such that the head or pressure level of water when released from the bag is sufficient to flow through the delivery line and speculum 22 into the colon of the patient. The speculum 22 is inserted up to the collar or anal ring 24 and the cuff 23 is inflated to an extent sufficient to prevent the speculum 22 from accidentally slipping out of the rectum during the bowel evacuation procedure. Once inflated to the desired extent, the air line 26 is closed off with a suitable form of closure clip to maintain the cuff 23 in the inflated condition. The collection bag 35 lays flat on the bottom of the box 36 and the drain hose 33 extends into one end of the box 36 for attachment into the collection bag 35. The delivery hose 17 is connected from the water bag 12 into the speculum 22 as described, and the air pressure line 38 is connected via branch lines 39 and 40 to the valves 16 and 32, respectively.

The squeeze bulb 28 is held in one hand and, by compressing or squeezing, will simultaneously pressurize the bag 54 to open the valve member 16 and the bag 77 to close the valve member 32. Water will then flow from the water bag through the delivery line into the patient until the bulb 42 is released to relieve pressure on the bags 54 and 77 whereupon the valve member 16 will return to a closed position to interrupt the flow of water from the bag 12. Simultaneously, the pressure in the colon will be sufficient to overcome any remaining pressure in the bag 77 so that the water and any waste material will flow through the drain line 30 into the collection bag 35. Most desirably, the collection bag 35 is placed below the level of the patient so as to encourage complete emptying of the colon. Further, a vacuum breaker may be employed in the drain line 30 or speculum 22 to avoid creation of a vacuum within the colon when it is being emptied.

The construction and arrangement of the elements making up the system 10 are such that the speculum 22, drain line 30 and collection bag 35 are disposable and can be removed or disconnected from the other elements of the system and replaced without disturbing or affecting the other elements of the system. The box 36 preferably is of generally rectangular configuration and sized to permit convenient storage of the entire assembly when not in use. The box includes upper flap portions, not shown, with hand grips in each flap portion so that the box can be readily opened, carried from place to place or conveniently stored by closing the flap portions into overlapping relation to one another over the collection bag 35.

In the form illustrated in FIG. 1, a check valve including a manually depressible vent may be disposed in the line 38 adjacent to the outlet side of the bulb 42 so that the bulb does not have to be held in the compressed position; instead, the check valve would be manually depressed to relieve air pressure in the line and permit it to escape through a suitable vent.

DETAILED DESCRIPTION OF MODIFIED FORM OF INVENTION

A modified form of invention is illustrated in FIG. 7 wherein like parts to those of FIG. 1 are correspondingly enumerated with prime numerals. In the modified form, a water source 12' may be of the type described in the preferred form; namely, a water bag 12 having a delivery hose 17' leading from the lower end of the bag 12 into a speculum 22' and having a modified form of check or closure valve 90 in the delivery line 17'. The speculum or rectal insertion tube 22' is of conventional construction, such as, of the type described in U.S. Pat. No. 5,019,056 and includes a coupling end 60' releasably connected to a modified form of valve member 92 in drain line 30' the drain line leading into a collection bag, not shown, within a storage box 36'. Air under pressure is supplied by a compressor 94 through valve control means in the form of a four-way valve 96 in which air pressure lines 39' and 40' lead to the valve members 90 and 92, respectively. One suitable form of compressor is Model Grant 14V-AC/PC 14 VAC Power Cartridge manufactured and sold by Grant Manufacturing Corporation of Vanderbilt, Michigan; and a suitable form of control valve 96 is MAC Part #45A-BA1-PFAA-1BA manufactured by MAC Valves, Inc. of Wixom, Mich.

The modified form of check valve 90 is made up of an elongated hollow cylindrical valve body 100 having inlet and outlet bores at opposite ends for insertion of an inlet coupling 102 and outlet coupling 103, respectively, in the delivery line 17'. An elastomeric liner 104 has opposite ends stretched over inner confronting ends of the couplings 102 and 103 and is directly responsive to air pressure applied to the line 39' to open and close the delivery line 17'. In addition, the outlet coupling 103 includes a check valve 106 to prevent the reverse flow of liquid from the speculum 22' through the delivery line 17'.

The modified form of valve member 92 substantially corresponds to the form of valve 32 shown and described in FIGS. 4-6 of the preferred form and includes an outer valve body or casing 65' corresponding to that of the preferred form in all respects except for elimination of the inflatable bag 77; instead, air pressure is applied directly through the branch line 40' into the port 108 of the valve body 65' to act directly upon the liner 58' to close the valve. When air pressure is removed from the line 40', the liner 58' will return to its open position.

In operation, the valve 96 may be manually controlled by the patient or an operator to regulate the supply of air under pressure from the compressor 94 to the lines 39' and 40'. Thus, when the control valve 96 establishes communication between the compressor 94 and the line 39', air pressure will cause the liner 104 in the valve 90 to close and prevent the flow of water from the water source 12' into the speculum 22'. When air under pressure is applied by the compressor 94 into the valve 92 via line 40', it will close off the flow of any water and waste material from the speculum 22' through the drain line 30'. Typically, the patient or operator would therefore maintain the valve in an open position to the pressure line 40' and close the control valve 96 to the line 39' so that the valve 90 would remain open for the delivery of water under pressure into the speculum 22' while the valve 92 is in the closed position. Conversely when it is desired to interrupt the flow of water to the speculum, line 39' would be pressurized and, to drain the waste matter from the colon, line 40' would be depressurized by closing the valve 96 to that line.

As a suitable alternative to the preferred form of invention shown in FIG. 1, separate squeeze bulbs can be employed in place of the flow control valve 96, each squeeze bulb connected to one of the air delivery lines 39' and 40' to independently control opening and closing of the valves 90 and 92. Air pressure through each line 39' and 40' is controlled by manually squeezing each bulb to apply pressure and holding the bulbs in a compressed condition so long as pressure is to be applied. The bulbs are composed of a rubber or rubber-like material so that when manual pressure on the bulbs is relaxed, the bulbs will automatically expand to create a vacuum or suction in the line to remove air pressure from an associated valve 90 or 92 and cause it to return to its former state or position. For example, when the bulb on the pressure line 39' is squeezed to open the value 90, water will flow through the speculum until the bulb is released. Similarly, by squeezing the bulb attached to the line 40', the valve 92 is closed to prevent flow through the drain line while water under pressure is being supplied through the speculum 22'. When the bulb in line 40' is released, the valve will return to its normally closed state or position to interrupt delivery of water into the colon and the valve 92 will return to its open position permitting flow of water and waste material from the colon through the drain line 30' into the collection bag.

DESCRIPTION OF ANOTHER MODIFIED FORM OF INVENTION

In FIGS. 8 and 9, like parts to those of FIG. 7 are correspondingly enumerated and is specifically directed to a dual valve assembly 112 having cutoff valve members 113 and 114 disposed in closely spaced, parallel relation to one another within a generally rectangular casing 115, and a common valve actuating member 116 is disposed between the valves 113 and 114 to alternately control opening and closing of the valves 113 and 114. The valve 113 is substituted for the valve 90 for the purpose of directing water from the delivery line 17' through the speculum 22' and includes an elastomeric liner 104 which has opposite ends stretched over inner confronting ends of the coupling 102 and 103. In turn, the valve member 114 establishes communication on the drain side of the system between the speculum 22' and drain line 30', in place of the valve 92. The valve 114 includes an elastomeric tubular liner 58' disposed within the body or casing 115 in facing relation to the valve 113. Although not illustrated in FIGS. 8 and 9, the liner 58' is stretched over end portions 59' to complete the connection between the speculum 22' and drain line 30'. The actuating member 116 is disposed between the valves 113 and 114 and includes a pneumatic cylinder 122 with a common air pressure line 123 leading from a squeeze bulb 120. A piston 124 is movable within the cylinder 122 and is pivotally connected to link arm 125 to extend between a retracted position as shown in FIG. 8 and extended position as shown in FIG. 9. In the retracted position, the piston 124 will cause toggle arm 126 to pivot about a fixed pivot 127 in a direction such that extension arm 128 will move into engagement with the liner 104, as shown in FIG. 9, to close the valve. When the plunger or piston 124 is extended, as shown in FIG. 8, it will cause the arm 126 to pivot about lower pivotal end 127 in a direction retracting or withdrawing the arm 128 away from engagement with the liner 104 and moving extension arm 130 into engagement with the liner 58' thereby closing the drain side of the system and opening the inlet or fill side. A toggle spring 132 has a lower end anchored as at 133 to the body or casing 115 of the valve and an upper end anchored at 134 to the toggle arm 126 so that as the piston drives the toggle arm 126 past center in either direction with respect to the pivotal end 127 the spring will assist in urging the extension arm 128 or 130 into the closed position with respect to each respective valve 113 and 114. In this relation, the extension arms 128 and 130 are configured to correspond to the cross-sectional configuration of the inner wall surfaces of the casing 115 when moved into the closed position so as to completely close or seal off the liner at that point.

In a manner corresponding to that described in relation to FIG. 7, air under pressure from the compressor 94 into the cylinder 122 will cause the toggle arm 126 to advance to a position closing the drain valve 114. Conversely, when air pressure is removed from the cylinder 122 causing the piston to return to the retracted position shown in FIG. 9, the toggle arm 126 will advance into a position closing the valve 113 while opening the valve 114. Once again, application of pressure may be regulated with the assistance of a flow control valve 96 interposed between the compressor 94 and actuator 116 in place of the squeeze bulb 120 connected to the line 123.

It is therefore to be understood that while preferred and modified forms of the present invention have been herein set forth and described, the above and other modifications and changes may be made without departing from the spirit and scope of the present invention as defined by the present claims and reasonable equivalents thereof.

We claim:

1. Bowel evacuation apparatus for the removal of waste material form the colon comprising in combination:

a source of water under pressure including a delivery line and first valve means for opening and closing said delivery line;

a rectal insertion tube in communication with said delivery line for directing water from said water source into said colon;

a drain line in communication with said tube including second valve means for selectively opening and closing said drain line; and valve control means for simultaneously controlling said first and second valve means whereby to open said first valve means for the delivery of water from said water source through said rectal insertion tube and to close said second valve means while said first valve means is open, said valve control means including an air pressurizing member and air pressure control lines connected to said first and second valve means.

2. Bowel evacuation apparatus according to claim 1, said valve control means operative to simultaneously close said first valve means and open said second valve means whereby to prevent water from flowing from said water source into said rectal insertion tube when water and waste material are removed from the colon for flow through said rectal insertion tube and said drain line.

3. Bowel evacuation apparatus according to claim 1, said first valve means being responsive to air pressure from said pressurizing member for opening and closing said delivery line.

4. Bowel evacuation apparatus according to claim 1, said second valve means being responsive to pressure from said pressurizing member for opening and closing said drain line.

5. Bowel evacuation apparatus according claim 1, said valve control means including said pressurizing member operative to simultaneously control opening and closing of said first and second valve means.

6. Bowel evacuation apparatus according to claim 5, said pressurizing member defined by at least one manual squeeze bulb.

7. Bowel evacuation apparatus according to claim 6, including pressure release means associated with said pressurizing member for simultaneously closing said first valve means and opening said second valve means.

8. Bowel evacuation apparatus according to claim 7, said first valve means including a check valve.

9. Bowel evacuation apparatus according to claim 8, said first valve means including a pivotal valve element and an inflatable member for moving said valve element between the open and closed positions in response to air pressure from said pressurizing member.

10. Bowel evacuation apparatus according to claim 9, said second valve means being movable to a closed position in response to air pressure from said valve control means.

11. Bowel evacuation apparatus according to claim 10, said second valve means including an elastomeric liner defining a passageway for the flow of liquid therethrough, and means for selectively constricting said liner to prevent the flow of liquid therethrough.

12. Bowel evacuation apparatus according to claim 11, said constricting means defined by an inflatable member movable into engagement with an external surface portion of said liner.

13. Bowel evacuation apparatus according to claim 2, said valve control means including a flow control valve.

14. Bowel evacuation apparatus according to claim 13, said flow control valve being a four-way flow control valve.

15. Bowel evacuation apparatus according to claim 13, said valve control means including a source of air under pressure in communication with said flow control valve.

16. Bowel evacuation apparatus according to claim 13, said valve control means including air pressure control lines extending from said flow control valve to said first and second valve means.

17. Bowel evacuation apparatus according to claim 13, said first valve means being a normally open valve which is responsive to air under pressure from said pressurizing member to move to a closed position.

18. Bowel evacuation apparatus according to claim 13, said second valve means being a normally open valve which is responsive to air under pressure from said pressurizing member to move to a closed position.

19. Bowel evacuation apparatus for extracting waste material from the colon comprising in combination:
a source of water under pressure, including a delivery line and first valve means for opening and closing said delivery line;
a speculum including an inlet port in communication with said delivery line;
a drain line in communication with said speculum including second valve means for selectively opening and closing said drain line; and
valve control means including pressurizing means for simultaneously controlling said first and second valve means in order to open said first valve means for the delivery of water from said water source through said speculum and to close said second valve means when said first valve means is open, and air pressure lines connected to said first and second valve means to simultaneously close said first valve means and open said second valve means in order to prevent water from flowing from said water source into said speculum when water and waste material are being removed from the colon through said speculum and said drain line.

20. Bowel evacuation apparatus according to claim 19, said water source being a water bag mounted above the level of the patient.

21. Bowel evacuation apparatus according to claim 19, said first valve means being responsive to air pressure from said pressurizing member for opening and closing said delivery line.

22. Bowel evacuation apparatus according to claim 19, said second valve means being responsive to air pressure from said pressurizing member for opening and closing said drain line.

23. Bowel evacuation apparatus according to claim 19, said pressurizing means including a manual squeeze bulb and air pressure control lines extending from said squeeze bulb to each of said first and second valve means.

24. Bowel evacuation apparatus according to claim 19, said first valve means being a normally open valve responsive to air under pressure from said pressurizing member to move to a closed position, and said second valve means being a normally open valve responsive to air under pressure from said pressurizing member to move to a closed position.

25. Bowel evacuation apparatus according to claim 19, said first valve means being a check valve including a pivotal valve element and an actuating member for moving said valve element between the open and closed positions in response to air pressure from said pressurizing means.

26. Bowel evacuation apparatus according to claim 25, said second valve means being movable to the closed position in response to air pressure from said pressurizing means.

27. Bowel evacuation apparatus according to claim 26, said second valve means including an elastomeric liner defining a passageway for the flow of liquid therethrough, and inflation means movable into engagement with an external surface portion of said elastomeric liner to constrict said liner and prevent the flow of liquid therethrough.

28. Bowel evacuation apparatus according to claim 19, wherein said pressurizing means includes a source of air under pressure, a flow control valve communicating with said source of air under pressure, and air control lines extending from said flow control valve to said first and second valve means.

29. Bowel evacuation apparatus according to claim 19, including a dual valve assemble containing said first and second valve means and a common actuator member therebetween.

30. Bowel evacuation apparatus according to claim 29, each of said first and second valve means comprising an elastomeric liner defining a passageway for the flow of liquid therethrough and disposed in spaced parallel relation to one another, and said actuator member including a toggle arm pivotal between a first position closing said first valve means and a second position closing said second valve means.

31. Bowel evacuation apparatus according to claim 30, said toggle arm including a pair of extension arms diverging away from a free end of said toggle arm, one of said extension arms movable into engagement with said liner of said first valve means when said toggle arm is pivoted to the first position, and another of said extension arms movable into engagement with said liner of said second valve means when said toggle arm is pivoted to the second position.

32. Bowel evacuation apparatus according to claim 31, each of said extension arms movable in a direction transverse to the flow of liquid through said liner whereupon engagement with each of said liners will constrict each respective liner to prevent the flow of liquid therethrough.

* * * * *